United States Patent [19]

Imaizumi et al.

[11] Patent Number: 5,559,079
[45] Date of Patent: Sep. 24, 1996

[54] HERBICIDAL COMPOSITION FOR THE CONTROL OF ANNUAL BLUEGRASS COMPRISING XANTHOMONAS CAMPESTRIS AND SULFONYLUREA HERBICIDES

[75] Inventors: Seiko Imaizumi; Masao Yamada; Tomoki Nishino, all of Yokohama, Japan

[73] Assignee: Japan Tobacco Inc., Tokyo, Japan

[21] Appl. No.: 365,421

[22] Filed: Dec. 28, 1994

[30] Foreign Application Priority Data

Dec. 28, 1993 [JP] Japan .................. 5-336655

[51] Int. Cl.⁶ ................... A01N 63/00; A01N 43/50; A01N 43/54; A01N 43/56
[52] U.S. Cl. ........................... 504/117; 504/136
[58] Field of Search ..................... 504/117, 136

[56] References Cited

U.S. PATENT DOCUMENTS

| | | | |
|---|---|---|---|
| 3,901,687 | 8/1975 | Bailey | 71/120 |
| 5,071,469 | 12/1991 | Artz | 71/92 |
| 5,077,045 | 12/1991 | Roberts | 424/93 |
| 5,192,541 | 3/1993 | Savage et al. | 424/93 |
| 5,271,932 | 12/1993 | Savage | 424/93 R |
| 5,332,673 | 7/1994 | Harris et al. | 435/253.3 |

FOREIGN PATENT DOCUMENTS

| | | |
|---|---|---|
| 0184385 | 6/1986 | European Pat. Off. . |
| 0207653 | 1/1987 | European Pat. Off. . |
| 0532206 | 3/1993 | European Pat. Off. . |
| 5-268946 | 10/1993 | Japan . |
| WO88/01172 | 2/1988 | WIPO . |
| WO91/03161 | 3/1991 | WIPO . |

OTHER PUBLICATIONS

Tomoki Nishino et al., Bacterial wilt of annual . . . , Annual Meeting of the Phytopathological Society of Japan, Apr. 3–5, 1994.
Seiko Imaizumi et al., Control of Annual Bluegrass with Bioherbicide, Weed Research, pp. 42–43 (1994).
Seiko Imaizumi et al., Control of Annual Bluegrass with Bioherbicide, Weed Research, pp. 40–41 (1994).
R. I. Gvozdyak et al., Effect of herbicides on the susceptibility of cabbage . . . Chemical Abstracts, Abstract No. 151715d, vol. 94, No. 19, 1981.
A. C. Hayward, The hosts of *Xanthomonas,* Department of Microbiology, The University of Queensland, pp. 1–15 1993.

*Primary Examiner*—S. Mark Clardy
*Attorney, Agent, or Firm*—Birch, Stewart, Kolasch, & Birch, LLP

[57] ABSTRACT

The present invention relates to a herbicidal composition for the control of annual bluegrass, comprising a microorganism having an ability to control annual bluegrass and belonging to the genus Xanthomonas, and a sulfonylurea compound. The composition of the present invention shows excellent herbicidal activity against annual bluegrass and broad-leaved weeds, and is extremely useful as a herbicide for turf.

11 Claims, No Drawings

HERBICIDAL COMPOSITION FOR THE CONTROL OF ANNUAL BLUEGRASS COMPRISING XANTHOMONAS CAMPESTRIS AND SULFONYLUREA HERBICIDES

BACKGROUND OF THE INVENTION

1. Field of the Invention

The present invention relates to a herbicidal composition for the control of annual bluegrass (*Poa annua*) comprising a microorganism belonging to the genus Xanthomonas.

2. Prior Art

Annual bluegrass which is growing abundantly at golf courses, city parks, athletic grounds and the like is the most strong, harmful weed in the turf. This weed is widely distributed throughout the world. In particular, annual bluegrass mixed in with the turf of golf courses, such as putting greens, tee grounds, fairways and roughs, comes into ears at all times in spite of frequent mowing, and scatters a large quantity of seeds into the turf all the year round. At present, there are a number of herbicides developed for control of annual bluegrass.

However, the effects of these chemical herbicides are very unstable at the site of use, and this has led to an increase in the amount of use and the frequency of application of these chemicals. The abundant use of agricultural chemicals at golf courses has particularly become a big social problem as one of the causes of environmental pollution. Among these chemical herbicides, there is no foliar treatment agent which can selectively kill annual bluegrass mixed in with Western turfgrasses, such as bentgrass, without harming the desired turfgrasses. Therefore, for the maintenance of bent green, manual weeding or even total renewal of turf is inevitably required, and the burden of costs therefor is tremendous.

On the other hand, microbial herbicides are being developed in the United States and Japan which comprise a bacterial pathogen to a plant, *Xanthomonas campestris,* and which selectively controls annual bluegrass without polluting the environment. Furthermore, a mixed application of *Xanthomonas campestris* and a chemical agent [a plant growth regulator, mefluidide (Embark™)] for enhancing the herbicidal effect of the microbial herbicide has also been disclosed [Japanese Unexamined Patent Publication (Kohyo) No. 63- 502438, U.S. Pat. No. 5,192,541].

However, the method of the prior art wherein the bacterial pathogen, *Xanthomonas campestris,* and the plant growth regulator are mixed and applied together has not solved at all a problem of herbicial spectrum which is the greatest advantage and, at the same time, a drawback of microbial herbicides, though this process can control annual bluegrass effectively. In other words, this prior art process can control only annual bluegrass.

OBJECTS AND SUMMARY OF THE INVENTION

It is the object of the present invention to solve the problem of herbicidal spectrum of microorganisms belonging to the genus Xanthomonas, and to enhance the ability of those microorganisms to control annual bluegrass.

The present inventors have found that the addition of a sulfonylurea compound exhibiting herbicidal activity against broad-leaved weeds to a microorganism having an ability to control annual bluegrass and belonging to the genus Xanthomonas can not only expand the herbicidal spectrum to broad-leaved weeds, but also remarkably improve the ability of the microorganism to control annual bluegrass. The present invention has been accomplished based on this finding.

According to the present invention, there is provided a herbicidal composition for the control of annual bluegrass, comprising a microorganism having an ability to control annual bluegrass and belonging to the genus Xanthomonas, as well as a sulfonylurea compound. Examples of microorganisms having an ability to control annual bluegrass and belonging to the genus Xanthomonas include microorganisms belonging to the species *Xanthomonas campestris.* More concretely, *Xanthomonas campestris* strains P-482, P-484 and the like may be cited. Examples of sulfonylurea compounds to be used in the present invention include imazosulfuron, flazasulfuron, pyrazosulfuron-ethyl, benzosulfuron-methyl and the like.

DETAILED DESCRIPTION OF THE INVENTION

Now the present invention will be described in more detail.

The microorganism to be used for the present invention is not particularly limited as long as it belongs to the genus Xanthomonas and has an ability to control annual bluegrass. Preferably, a microorganism belonging to the species *Xanthomonas campestris* is used. Preferable strains of *Xanthomonas campestris* include P-482, P-484, P-481, P-485, P-496, P-497, P-498, P-499, P-500, P-515, P-516 and P-517. These strains have been isolated from the internal parts of plant bodies of naturally growing annual bluegrass.

Out of the above strains, P-482 shows the following bacteriological properties.

Bacteriological properties of P-482

| Chemical substance | Decomposing ability |
|---|---|
| α-Cyclodextrin | + |
| Dextrin | + |
| Glycogen | + |
| Tween 40 | + |
| Tween 80 | + |
| N-acetyl-D-galactosamine | − |
| N-acetyl-D-glucosamine | + |
| Adonitol | − |
| L-arabinose | + |
| D-arabitol | − |
| Cellobiose | + |
| i-Erythritol | − |
| D-fructose | + |
| L-fucose | + |
| D-galactose | + |
| Gentiobiose | + |
| α-D-glucose | + |
| m-Inositol | − |
| α-D-lactose | + |
| Lactulose | + |
| Maltose | + |
| D-mannitol | − |
| D-mannose | + |
| D-melibiose | − |
| B-methyl-D-glucoside | − |
| D-psicose | + |
| D-raffinose | − |
| L-rhamnose | − |
| D-sorbitol | − |
| Saccharose | − |
| D-trehalose | + |
| Turanose | UN |
| Xylitol | − |
| Methyl pyruvate | + |

-continued

Bacteriological properties of P-482

| Chemical substance | Decomposing ability |
|---|---|
| Monomethyl succinate | + |
| Acetic acid | + |
| cis-Aconitic acid | − |
| Citric acid | − |
| Formic acid | − |
| D-lactone galactonate | − |
| D-galactonic acid | − |
| D-gluconic acid | − |
| D-glucosamic acid | − |
| D-glucuronic acid | − |
| α-Hydroxybutyric acid | + |
| β-Hydroxybutyric acid | − |
| γ-Hydroxybutyric acid | − |
| ρ-Hydroxyphenylacetic acid | − |
| Itaconic acid | − |
| α-Ketobutyric acid | + |
| α-Ketoglutaric acid | + |
| α-Ketovaleric acid | − |
| D, L-lactic acid | + |
| Malonic acid | − |
| Propionic acid | − |
| Quinic acid | − |
| Sebacic acid | − |
| Succinic acid | + |
| Bromosuccinic acid | + |
| Succinamide | + |
| Glucuronamide | − |
| Alaninamide | + |
| D-alanine | + |
| L-alanine | + |
| L-alanyl-glycine | + |
| L-asparagine | − |
| L-aspartic acid | UN |
| L-glutamic acid | + |
| Glycyl-L-aspartic acid | − |
| Glycyl-L-glutamic acid | + |
| L-histidine | − |
| Hydroxy-L-proline | + |
| L-leucine | − |
| L-ornithine | − |
| L-phenylalanine | − |
| L-proline | − |
| L-pyroglutamic acid | − |
| D-serine | − |
| L-serine | + |
| L-threonine | − |
| D, L-carnitine | − |
| γ-Aminobutyric acid | − |
| Urocanic acid | − |
| D-saccharic acid | − |
| Inosine | − |
| Urdine | − |
| Thymidine | − |
| Phenylethylamine | − |
| Putrescine | − |
| 2-Aminoethanol | − |
| 2,3-Butanediol | − |
| Glycerol | + |
| D, L- α-glycerolphosphate | + |
| Glucose-1-phosphate | + |
| Glucose-6-phosphate | + |

+: can assimilate the substance
−: cannot assimilate the substance
UN: The results were unstable in repeated tests.

The above results were obtained by using Biolog GN MicroPlate™ manufactured by Biolog Inc. As a result of a data base survey using Microlog™ Software of Biolog Inc. for identifying microorganisms, P-482 which has the above-mentioned properties was identified as a microorganism belonging to the species *Xanthomonas campestris*. Surveys were conducted for the other strains according to similar procedures, and all of them were identified as microorganisms belonging to the species *Xanthomonas campestris.* Incidentally, the two strains of P-482 and P-484 were deposited with National Institute of Bioscience and Human Technology, Agency of Industrial Science and Technology, Tsukuba-shi, Japan, under accession Nos. FERM BP-4431 and FERM BP-4430, respectively, on Oct. 1, 1993.

No special methods are required for the cultivation of the microorganism to be used for the present invention. The microorganism can be cultivated according to conventional methods. Either a synthetic medium or a natural medium may be used as long as it appropriately contains assimilable carbon source and nitrogen source, inorganic substances and necessary growth promoting substances. For example, YNB (yeast and meat broth) medium or NA (nutrient agar) medium may be used. During the cultivation, it is preferred that the temperature be kept at 5°–40° C., preferably 28°–31 ° C., and pH at 5–9, preferably 6–7. When the microorganism has been grown for 2 to 4 days under such conditions, a sufficient amount of cells can be obtained. In the preparation of the composition of the present invention, the use of cells themselves is preferable. The cells are obtained by centrifugation of cultures of the microorganism.

The sulfonylurea compound to be used for the present invention is not particularly limited, as long as the compound has the following structure and shows herbicidal effect on broad-leaved weeds:

$R_1$ —$SO_2$ —NH—CO—NH—$R_2$ (wherein $R_1$ and $R_2$ are any compounds.) Examples of such sulfonylurea compounds include bensulfuron, chlorimuron, cinosulfuron, flazasulfuron, imazosulfuron, nicosulfuron, primisulfuron, pyrazosulfuron, thifensulfuron, tribehuron, triasulfuron, and methyl or ethyl esters thereof. Among all of these compounds, it is preferable to use imazosulfuron, flazasulfuron, pyrazosulfuron-ethyl, bensulfuron-methyl and the like. In the composition of the present invention, one of these compounds may be used alone, or plurality of them may be used in combination. By the way, these sulfonylurea compounds have herbicidal effect upon broad-leaved weeds, but they scarcely show this effect upon those weeds belonging to the genus Poa, such as annual bluegrass.

When the composition of the present invention is used as a herbicide, it can be used as a liquid formulation suspended in water. In this case, a spreader or the like may be added, if necessary. If the composition is used as a liquid formulation, the microorganism concentration is $10^1$–$10^{11}$ CFU/ml, preferably $10^6$–$10^{10}$ CFU/ml, and more preferably $10^7$–$10^{10}$ CFU/ml. If the concentration is over $10^{11}$ CFU/ml, the viscosity of the composition increases so much that the use thereof becomes uneasy. If the concentration is below $10^3$ CFU/ml, the herbicidal effect thereof remarkably decreases. However, if the microorganism of the present invetion is used at a low concentration of $10^3$ CFU/ml or below, it reveals the activity of a plant growth regulator against annual bluegrass. In other words, when applied at a low concentration, the microorganism of the present invention promotes the growth of culms of annual bluegrass before seeds thereof attain maturity. This means that the seeds of annual bluegrass are removed by mowing before they fall upon the turf. This activity as a plant growth regulator works effectively even at low temperatures where the herbicidal effect of the microorganism is relatively suppressed. The concentration of the sulfonylurea compound is 0.001–0.1% by weight, preferably 0.01–0.05% by weight, for imazosulfuron; 0.1–100 ppm, preferably 0.5–50ppm for flazasulfuron; 0.1–50 ppm, preferably 1–10 ppm for pyrazosulfuron-ethyl; and 0.01–0.25% by weight, preferably 0.1–0.25% by weight, for bensulfuron-methyl. In addition, the herbicide of the present invention can be used as a dust formulation, not limited to water suspension.

When the composition of the present invention is applied to an actual field, the composition is used in a manner so that the microorganism concentration becomes $10^{11}$–$10^{10}$ CFU per 10 ares of the field, and the concentration of sulfonylurea compound 10–100 g per 10 ares of the field for imazosulfuron and 0.025–7.5 g for flazasulfuron.

The target weeds to be controled by the composition of the present invention are annual bluegrass, purple nutsedge, dandelion and the like, and the composition of the present invention does not reveal any pathogenicity to major turfgrasses grown at golf courses, such as bentgrass, Kentucky bluegrass, perennial ryegrass, Italian ryegrass, Bermuda grass, tall oatgrass, timothy grass, tall rescue, red rescue, chewing rescue and hard rescue, as well as other gramineous crops.

DETAILED DESCRIPTION OF PREFERRED EMBODIMENTS

The present invention will now be described in more detail with reference to the following Test Examples and Examples, which should not be construed as limiting the scope of the present invention.

(Test Example 1) The isolation, selection and identification of microorganisms

Annual bluegrass (*Poa annua*) plants growing at golf courses, parks and the like were collected. After damaged tissues were removed from the plant samples, leaf or stem sections 1 cm in length were prepared. They were surface sterilized by dipping into 70% ethanol solution for 1 minute and then washing with sterile distilled water. The surface sterilized sections were milled in 200 μl of sterile distilled water, then streaked onto an ordinary agar medium (NA medium) and incubated in an incubator at 28° C. By the above operations, only those bacteria which exist inside of the plant bodies can be separated.

Such colonies that resemble Xanthomonas bacteria were selected from the colonies appeared on the agar medium during the incubation period. The thus selected colonies were suspended in a small amount of sterile distilled water. Scissors sterilized with 70% ethanol and flame were dipped in the resultant cell suspension. This suspension was inoculated into annual bluegrass seedlings which had been grown for about 1 month in a greenhouse by cutting the tip of their leaves with the above-mentioned scissors. About 3 weeks later, Xanthomonas bacteria were separated by similar procedures as mentioned above from those annual bluegrass plants whose symptoms of disease had been confirmed. These separated bacteria were inoculated into annual bluegrass plants again, and then the bacterial pathogens of annual bluegrass were separated from those plants which were confirmed to exhibit similar symptoms. As a result, 89 strains of Xanthomonas bacteria showing pathogenicity to annual bluegrass were obtained from 42 locations of 17 urban and rural prefectures in Japan. From these strains, 12 strains of annual bluegrass pathogens which have extremely strong virulence were screened. They are P-482 (FERM BP-4431), P-484 (FERM BP- 4430), P-481, P-485, P-496, P-497, P-498, P-499, P-500, P-515, P- 516 and P-517. All of those annual bluegrass plants which had been inoculated with the above 12 strains began wilting from the site of cutting 5 days after the inoculation, and 7 days after the inoculation their leaves as a whole wilted while maintaining a green color. Their plant bodies as a whole became white and died completely 10 days after the inoculation.

(Test Example 2) The pathogenicity of the isolated microorganisms to annual bluegrass Seeds of annual bluegrass (25 mg) were sown in Jiffy Pots (5 cm x 5 cm x 5 cm). The resultant seedlings were grown in a greenhouse for 3 weeks, and then used for inoculation test. Before inoculation, the plants were cut to a height of 2 cm with an electric mower. They were spray-inoculated with 0.5 ml per pot of cell suspensions of Xanthomonas bacteria of which the cell density had been adjusted at $10^9$ CFU/ml. The 12 strains of Xanthomonas bacteria [P-482 (FERM BP-4431), P-484 (FERM BP-4430), P-481, P-485, P-496, P-497, P-498, P-499, P-500, P-515, P-516 and P-517] used for this test had been respectively grown in advance on YNB (yeast/meat broth) medium at 28° C. for 20 hours. Then, 1 ml each of these cultures were transferred to 100 ml of YNB medium, where they were further cultivated under shaking at 28° C. After 22 hours, the cultures were centrifuged at 5000 rpm for 15 minutes to thereby obtain a pellet. The pellet was then diluted with sterile distilled water, and the $OD_{575}$ thereof was measured. Inoculation sources of the predetermined cell density were obtained by calculating 0.1 in absorbance as 1 x $10^8$ ODU/ml. Incidentally, 100 μl of the serially diluted inoculation source was spread on an NA (nutrient agar) plate, which was then left in an incubator at 28° C. for 3 days. The accurate viable bacterial count (CFU/ml) was obtained by counting the number of colonies appearing on the plate. As a control standard, plants were spray-inoculated with the equal amount of distilled water. The inoculated plants were placed in a greenhouse at 25°/20° C. (day temperature/night temperature). After 3 weeks from the inoculation, the plants were observed for disease symptoms, and the virulence of each strain was compared with each other.

The pathogenicity of Xanthomonas strains to annual bluegrass

| | |
|---|---|
| P-481 | +++ |
| P-482 | +++ |
| P-484 | +++ |
| P-485 | +++ |
| P-496 | +++ |
| P-497 | +++ |
| P-498 | +++ |
| P-499 | +++ |
| P-500 | +++ |
| P-515 | +++ |
| P-516 | +++ |
| P-517 | +++ |
| Control (treated with sterile distilled water) | – |

+++: Death
–: No symptoms observed

As a result, P-482 (FERM BP-4431), P-484 (FERM BP-4430), P-481, P-485, P-496, P-497, P-498, P-499, P-500, P-515, P-516 and P-517 withered and killed annual bluegrass completely.

(Test Example 3) Assay of the safety of Xanthomonas strains to major turfgrasses, gramineous plants and useful crops.

Seeds of major turfgrasses, gramineous plants and useful crops were sown in small pots (30 cm x 10 cm x 5 cm) for raising seedlings. For dicotyledonous plants, those grown up to 3 to 5 true leaves were used for the test. For monocotyledonous plants, those grown up to 3 to 5 leaves were used for the test. In substantially the same manner as described in Test Example 2, cell suspensions of P-482 and P-484 were prepared and adjusted to give a cell density of $10^9$ CFU/ml. Sterilized scissors were dipped into these cell suspensions, and used to cut turfgrass seedlings to a height of 2 cm. For the other plants, bundles of sterilized needles (7 needles forming a bundle) which had been dipped into the suspensions were used for inoculation by perforation. The cell suspension was inoculated into the leaf vein (vascular bundle) of the most developed leaf and 2 other leaves located above it in each plant. Immediately after the inoculation, the plants were carried to a humid chamber with 100% humidity at 25° C. and left there overnight. Then, the plants were placed in a greenhouse at 25° C./20° C. (day temperature/night temperature). After 2 or 3 weeks, each plant was observed for disease symptoms, and the presence of pathogenicity to each plant was assayed. As control standards, all of the plants were sprayed with sterile distilled water and a similar assay was conducted. In addition, as comparative controls, annual bluegrass plants were inoculated with P-482 and P-484 by using sterilized scissors and needles, and the pathogenicity of these strains to annual bluegrass was confirmed. For each section, test was repeated 3 times.

The results are shown below.

|  | Plant | Pathogenicity | |
|---|---|---|---|
|  |  | P-482 | P-484 |
| Major turfgrasses | Bentgrass | − | − |
|  | Kentucky bluegrass | − | − |
|  | Perennial ryegrass | − | − |
|  | Italian ryegrass | − | − |
|  | Bermuda ryegrass | − | − |
|  | Tall oatgrass | − | − |
|  | Timothy grass | − | − |
|  | Tall fescue | − | − |
|  | Red fescue | − | − |
|  | Chewing fescue | − | − |
|  | Hard fescue | − | − |
| Gramineous crops | Rice | − | − |
|  | Barley | − | − |
|  | Wheat | − | − |
|  | Corn | − | − |
|  | Edible millet | − | − |
| Useful crops cultivated | Tobacco | − | − |
|  | Pumpkin | − | − |
|  | Cucumber | − | − |
|  | Carrot | − | − |
|  | Burdock | − | − |
|  | Spinach | − | − |
|  | Green onion | − | − |
|  | Onion | − | − |
|  | Soy bean | − | − |
|  | Garden pea | − | − |
|  | Cow pea | − | − |
|  | Kidney bean | − | − |
|  | Potato | − | − |
|  | Sweet potato | − | − |
|  | Taro | − | − |
|  | Tomato | − | − |
|  | Egg plant | − | − |
|  | Radish | − | − |
|  | Rape | − | − |
|  | Cabbage | − | − |
|  | Chinese cabbage | − | − |
|  | Turnip | − | − |
|  | Garland chrysanthemum | − | − |
|  | Lettuce | − | − |
|  | Mat rush | − | − |
|  | Japanese honewort | − | − |
|  | Violet | − | − |
|  | Lily | − | − |
|  | Carnation | − | − |
| Control | Annual bluegrass (Needle inoculation) | +++ | +++ |
|  | Annual bluegrass (Scissors inoculation) | +++ | +++ |

+++: Death
−: No symptoms observed

As a result, it was found that both P-482 and P-484 show no pathogenicity to those plants other than annual bluegrass.

(Test Example 4) The identification of microorganisms

Using a BIOLOG system, bacteriological characteristics were examined for the 12 strains (P-482, P-484, P-481, P-485, P-496, P- 497, P-498, P-499, P-500, P-515, P-516 and P-517 ) which were isolated in Test Example 1.

In the BIOLOG system, there are used Biolog GN MicroPlate™, a computer, and Microlog™ Software which is the data base and software for the identification of microorganisms. Biolog GN MicroPlate™ is a 96-well microtiter plate containing 96 kinds of chemicals (such as sugars, organic acids, amino acids and the like) to examine the characteristic assimilation of chemicals by microorganisms of interest. Now, the operational procedures for this system will be described briefly. First, each culture of the above-mentioned 12 strains which have been grown in advance is placed in all of the wells of Biolog GN MicroPlate™, and then grown for 1 to 3 days. If the strain has assimilated a chemical, a purple precipitate will be produced (an agent which will produce a precipitate under certain circumstances is also filled in the well). Then, the results obtained are input to the computer, and search command is given. Subsequently, the results of identification are automatically displayed.

(Test Example 5) The control effect of Xanthomonas bacteria on annual bluegrass 25 mg of annual bluegrass seeds were sown on the soil filled in a jiffy pot 5 cm x 5 cm x 5 cm (out of about 78 seeds, about 50 seeds germinated). Seedlings were grown in a greenhouse up to 3 to 4 leaves, and used for test during the third week from the sowing. The above-mentioned pot was made one section. For each experimental section, the test was repeated 6 times.

In substantially the same manner as described in Test Example 2, P-482 and P-484 cultures were adjusted with distilled water to give a cell density of $10^9$ CFU/ml. Each 3 ml of the thus prepared inoculation sources was spray-inoculated with a sprayer to 6 sections of annual bluegrass plants which had been cut to a height of 2 cm with an electric mower. As a control, sterile distilled water was similarly spray-inoculated to plants.

After the inoculation, the plants were carried to a greenhouse at 25° C./20° C. (day temperature/night temperature), and observed for the transition of disease symptoms. Control effect was judged by observing the appearance of the plants 2 weeks after the inoculation based on the following 6-grade rating. The results are shown as the average value from 6 repeated tests.

0: No influence upon the growth of plants
1: 20% or less of growth suppression by wilt
2: 20–40% of growth suppression by wilt
3: 40–60% of growth suppression by death or wilt
4: 60–80% of growth suppression by death or wilt
5: 80–99% of growth suppression by death or wilt
6: Complete death

| | Control | P-482 | P-484 |
|---|---|---|---|
| Control effect | 0 | 5.3 | 5.2 |

As a result, Xanthomonas strains of P-482 and P-484 pertaining to the present invention exhibited excellent herbicidal effect on annual bluegrass.

(Test Example 6) Safety to animals

With respect to the acute dermal toxicity and acute oral toxicity of P-482 on SD rats, $LD_{50}$ values are 2000 mg/kg or more and 5000 mg/kg or more, respectively, for male and female (according to the data measured by Institute of Environmental Toxicology). Its safety to animals has been proven.

EXAMPLE

The Herbicidal Effect of the Herbicidal Composition on Annual Bluegrass

Annual bluegrass seedlings and cells of Xanthomonas strain P- 484 were prepared in substantially the same manner as described in Test Example 5. A cell suspension of P-482 was prepared to give a cell density of $2 \times 10^8$ CFU/ml so that the density becomes $10^8$ CFU/ml when it is mixed with a sulfonylurea compound prepared in a 2-fold concentration. The sulfonylurea compound to be mixed in the composition was prepared in advance to give a 2-fold concentration. Imazosulfuron (Shibatait, a product of Takeda Chemical Industries Ltd.) was prepared so that its concentration becomes 0.05% and 0.01% when applied. Flazasulfuron (Shibagen, a product of Ishihara Sangyo Kaisha Ltd.) was prepared so that its concentration becomes 50 ppm, 5 pp and 0.5 ppm when applied.

An aliquot of the above-mentioned cell suspension was mixed with the equal amount of each of the sulfonylurea solutions to give a total volume of 3 ml. This mixture was spray-inoculated with a sprayer to annual bluegrass seedlings of 6 sections which had been cut to a height of 2 cm with an electric mower in advance. As a control, sterile distilled water was similarly spray-inoculated to plants.

Since the growth rate of Xanthomonas bacteria vary depending on temperatures and thus their herbicidal effects vary, the temperature in greenhouses was set at 3 grades, and the influence thereof was also studied. In other words, 3 greenhouses were used wherein the temperature (day temperature/night temperature) was set at 25° C./20° C., 20° C./15° C. and 15° C./10° C., respectively. In each greenhouse, inoculated plants were placed to observe the transition of disease symptoms. Control effect was judged with the average value from 6 repeated tests in the same manner as described in Test Example 6.

The test results are as follows.

TABLE 1

The Control Effect of a Composition comprising
Xanthomonas strain P-482 and Imazosulfuron (Shibatait)

| Imazosulfuron | P-482 | |
|---|---|---|
| (%) | 0 CFU/ml | $10^8$ CFU/ml |
| (1) 25° C./20° C. (day/night), evaluation after 2 weeks | | |
| 0 | Control effect 0 | Control effect 4.4 |
| 0.01 | Control effect 0 | Control effect 5.5 |
| 0.05 | Control effect 0 | Control effect 6.0 |
| (2) 20° C./15° C. (day/night), evaluation after 2 weeks | | |
| 0 | Control effect 0 | Control effect 2.3 |
| 0.01 | Control effect 0 | Control effect 2.4 |
| 0.05 | Control effect 0 | Control effect 5.3 |
| (3) 15° C./10° C. (day/night), evaluation after 3 weeks | | |
| 0 | Control effect 0 | Control effect 0 |
| 0.01 | Control effect 0 | Control effect 0 |
| 0.05 | Control effect 0 | Control effect 3.5 |

TABLE 2

The Control Effect of a Composition comprising
Xanthomonas strain P-484 and Flazasulfuron (Shibagen)

| Flazasulfuron | P-482 | |
|---|---|---|
| (ppm) | 0 CFU/ml | $10^8$ CFU/ml |
| (1) 25° C./20° C. (day/night), evaluation after 2 weeks | | |
| 0 | Control effect 0 | Control effect 4.3 |
| 0.5 | Control effect 0 | Control effect 6.0 |
| 5 | Control effect 0 | Control effect 6.0 |
| 50 | Control effect 2.2 | Control effect 6.0 |
| (2) 20° C./15° C. (day/night), evaluation after 2 weeks | | |
| 0 | Control effect 0 | Control effect 2.1 |
| 0.5 | Control effect 0 | Control effect 2.9 |
| 5 | Control effect 0 | Control effect 4.9 |
| 50 | Control effect 1.9 | Control effect 5.4 |

As Tables 1- (1), -(2) and -(3) show, the mixed composition of the present invention comprising Xanthomonas strain P-482 and 0.05% imazosulfuron exhibits a synergistic increase in herbicidal activity in a relatively wide temperature range of from 10° C. to 25° C., compared to the cases of the single application of either component.

As Tables 2-(1) and -(2) show, the mixed composition of the present invention comprising Xanthomonas strain P-484 and 5 ppm flazasulfuron exhibits a synergistic increase in herbicidal activity in a temperature range of from 15° C. to 25° C., compared to the cases of the single application of either component.

USE EXAMPLE

A Liquid Formulation comprising P-482 or P-484 and Imazosulfuron

At the time of mixing, a P-482 or P-484 culture was adjusted to give a cell density of $10^8$ CFU/ml and Shibatait was adjusted to give a concentration of 5 μl/ml (0.05% by weight as imazosulfuron). To the resultant mixture, 10 μl (0.01% by weight) of a surfactant, Silwet L-77, was added. Then, the mixture was diluted with distilled water to give a 100 ml liquid formulation. As test plants, there were used annual bluegrass (3 weeks from the sowing, which had been grown under the same conditions as described in Test Example 2), Korean lawn grass and bentgrass (both of which had been grown in a pot for about one year and then made turf). For each of the plants, inoculation was repeated 6 times using 6 Jiffy Pots (5 cm x 5 cm x 5 cm). Control effect was judged in the same manner as described in Test Example 5, taking the mean value. Before testing, annual bluegrass, Korean lawn grass and bentgrass were cut to a height of 2 cm with an electric mower. 3 ml of the above liquid formulation was spray-inoculated to each plant with a sprayer. As a control, plants were spray-inoculated with the equal amount of distilled water. The inoculated plants were placed in greenhouses wherein the temperature was set at 20° C./15° C. or 25° C./20° C. (day/night). Control effect was judged 2 weeks later. The results of this test are shown in Tables 3 and 4.

TABLE 3

The Effect of a Liquid Formulation comprising P-482

|  |  | Annual bluegrass | Korean lawn grass | Bent-grass |
|---|---|---|---|---|
| (1) 20°C./15 °C. (day/night) , evaluation after 2 weeks | | | | |
| Control | Control effect | 0 | 0 | 0 |
| Liquid formulation | Control effect | 4.2 | 0 | 0 |
| (2) 25° C./20° C. (day/night), evaluation after 2 weeks | | | | |
| Control | Control effect | 0 | 0 | 0 |
| Liquid formulation | Control effect | 6.0 | 0 | 0 |

TABLE 4

The Effect of a Liquid Formulation comprising P-484

|  |  | Annual bluegrass | Korean lawn grass | Bent-grass |
|---|---|---|---|---|
| (1) 20° C./15° C. (day/night), evaluation after 2 weeks | | | | |
| Control | Control effect | 0 | 0 | 0 |
| Liquid formulation | Control effect | 4.3 | 0 | 0 |
| (2) 25° C./20° C. (day/night), evaluation after 2 weeks | | | | |
| Control | Control effect | 0 | 0 | 0 |
| Liquid formulation | Control effect | 6.0 | 0 | 0. |

From the above results, it is clear that both liquid formulations respectively comprising P-482 and P-484 can kill annual bluegrass completely without giving any damage to bentgrass or Korean lawn grass.

The herbicidal composition of the present invention shows excellent herbicidal activity against annual bluegrass, and it also shows herbicidal activity against broad-leaved weeds. Therefore, the composition of the present invention is extremely useful as a herbicide for use at turf locations such as golf courses.

What is claimed is:

1. A process for the control of annual bluegrass, which comprises applying to annual bluegrass a herbicidal composition comprising a microorganism having an ability to control annual bluegrass and belonging to *Xanthomonas campestris,* and a sulfonylurea compound.

2. The process according to claim 1, wherein said microorganism belonging to the species *Xanthomonas campestris* is *Xanthomonas campestris* P-482 or *Xanthomonas campestris* P-484.

3. The process according to claim 1, wherein said sulfonylurea compound is imazosulfuron, flazasulfuron, pyrazosulfuron-ethyl or bensulfuron-methyl.

4. The process according to claim 1, wherein said herbicidal composition is a liquid formulation wherein the microorganism concentration is $10^1$–$10^{11}$ CFU/ml.

5. The process according to claim 4, wherein the microorganism concentration is more than $10^3$ CFU/ml.

6. The process according to claim 1, wherein the concentration of sulfonylurea is 0.001–0.1 weight percent.

7. The process according to claim 1, wherein the annual bluegrass to be controlled is *Poa annua.*

8. A process for controlling annual bluegrass, which comprises applying to annual bluegrass an effective amount of a herbicidal composition comprising a microorganism having an ability to control annual bluegrass and having all of the identifying characteristics of *Xanthomonas campestris,* and a sulfonylurea compound.

9. A herbicidal composition for controlling annual bluegrass, which comprises herbicidally effective amounts of *Xanthomonas campestris* having the ability to control annual bluegrass and a sulfonylurea compound.

10. The composition according to claim 9, wherein said microorganism belonging to the species *Xanthomonas campestris* is *Xanthomonas campestris* P-482 or *Xanthomonas campestris* P-484.

11. The composition according to claim 9, wherein said sulfonylurea compound is imazosulfuron, flazasulfuron, pyrazosulfuron-ethyl or bensulfuron-methyl.

\* \* \* \* \*